US012427190B2

United States Patent
Chen et al.

(10) Patent No.: US 12,427,190 B2
(45) Date of Patent: *Sep. 30, 2025

(54) VLP-BASED MONOVALENT EBOLA VACCINES AND METHODS OF MAKING AND USING SAME

(71) Applicants: Children's Hospital Medical Center, Cincinnati, OH (US); Xuemin Chen, Decatur, GA (US)

(72) Inventors: Xuemin Chen, Decatur, GA (US); Karnail Singh, Deerfield Township, OH (US); Paul Spearman, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 155 days.

This patent is subject to a terminal disclaimer.

(21) Appl. No.: 16/494,843

(22) PCT Filed: Mar. 28, 2018

(86) PCT No.: PCT/US2018/024758
§ 371 (c)(1),
(2) Date: Sep. 17, 2019

(87) PCT Pub. No.: WO2018/183443
PCT Pub. Date: Oct. 4, 2018

(65) Prior Publication Data
US 2020/0085937 A1    Mar. 19, 2020

Related U.S. Application Data

(60) Provisional application No. 62/477,480, filed on Mar. 28, 2017.

(51) Int. Cl.
*A61K 39/12*    (2006.01)
*C07K 14/08*    (2006.01)
*C12N 7/00*    (2006.01)
*A61K 39/00*    (2006.01)

(52) U.S. Cl.
CPC .............. *A61K 39/12* (2013.01); *C07K 14/08* (2013.01); *C12N 7/00* (2013.01); *A61K 2039/5258* (2013.01); *C12N 2740/10023* (2013.01); *C12N 2740/11023* (2013.01); *C12N 2740/12023* (2013.01); *C12N 2740/13023* (2013.01); *C12N 2740/14023* (2013.01); *C12N 2740/15023* (2013.01); *C12N 2740/16022* (2013.01); *C12N 2740/16023* (2013.01); *C12N 2760/14123* (2013.01); *C12N 2760/14134* (2013.01)

(58) Field of Classification Search
CPC ...... C07K 14/08; C07K 14/005; A61K 39/12; A61K 2039/5258; C12N 2740/10623; C12N 2760/14123; C12N 2740/10023; C12N 2740/11023; C12N 2740/12023; C12N 2740/13023; C12N 2740/14023; C12N 2740/15023; C12N 2740/16023; C12N 2760/14134

See application file for complete search history.

(56) References Cited

U.S. PATENT DOCUMENTS

| | | | |
|---|---|---|---|
| 9,045,727 B2 | 6/2015 | Compans et al. | |
| 9,597,388 B2 | 3/2017 | Weiner et al. | |
| 9,957,300 B2 | 5/2018 | Compans et al. | |
| 9,969,986 B2 | 5/2018 | Akahata et al. | |
| 2009/0210952 A1 | 8/2009 | Wu et al. | |
| 2010/0143406 A1 | 6/2010 | Smith et al. | |
| 2014/0004146 A1* | 1/2014 | Zhou ................. | A61P 31/18 435/69.3 |
| 2015/0266929 A1* | 9/2015 | Compans ............ | A61K 39/21 530/359 |
| 2015/0335726 A1* | 11/2015 | Weiner ............... | C07K 14/005 424/186.1 |

FOREIGN PATENT DOCUMENTS

| | | |
|---|---|---|
| WO | WO 2015/066715 A1 | 5/2015 |
| WO | WO 2016/168187 A1 | 10/2016 |
| WO | WO 2017/015457 A1 | 1/2017 |

OTHER PUBLICATIONS

Grant-Klein, R. J., et al., Aug. 2015, Codon-optimized filovirus DNA vaccines delivered by intramuscular electroporation protect cynomolgus macaques from lethal Ebola and Marburg virus challenges, Human Vacc. Immunother. 11(8):1991-2004.*
Falzarano, D., et al., 2011, Single Immunization With a Monovalent Vesicular Stomatitis Virus-Based Vaccine Protects Nonhuman Primates Against Heterologous Challenge With Bundibugyo ebolavirus, J. Infect. Dis. 204(Suppl. 3):S1082-S1089.*
Yonezawa, A., et al., Jan. 2005, Studies of Ebola Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha, J. Virol. 79(2):918-926.*
Agnandji, S.T., et al., "Phase 1 Trials of rVSV Ebola Vaccine in Africa and Europe—Preliminary Report," N Engl J Med, Apr. 2016, 374(17):1647-1660, 22 pgs.

(Continued)

*Primary Examiner* — Jeffrey S Parkin
(74) *Attorney, Agent, or Firm* — Frost Brown Todd LLP; Nicole M. Tepe

(57) ABSTRACT

Disclosed herein are virus-like particle (VLP)-based monovalent vaccine compositions. The compositions may comprise a spherical retroviral Group-specific Antigen ("Gag") protein core and a single Ebola glycoprotein selected from either a Zaire (EBOV) glycoprotein or a Sudan (SUDV) glycoprotein. The Ebola glycoprotein may be incorporated into the surface of the spherical Gag core, wherein said VLP-based vaccine presents a single Ebola glycoprotein antigen.

24 Claims, 6 Drawing Sheets
Specification includes a Sequence Listing.

(56) References Cited

OTHER PUBLICATIONS

Henao-Restrepo, A.M., et al., "Efficacy and effectiveness of an rVSV-vectored vaccine expressing Ebola surface glycoprotein: interim results from the Guinea ring vaccination cluster-randomised trial," Lancet, 2015, 386:857-866, 10 pgs.

Huttner, A., et al., "The effect of dose on the safety and immunogenicity of the VSV Ebola candidate vaccine: a randomised double-blind, placebo-controlled phase 1/2 trial," Lancet Infect Dis, 2019, 15(10):1156-1166, 25 pgs.

Kibuuka, H., et al., "Safety and immunogenicity of Ebola virus and Marburg virus glycoprotein DNA vaccines assessed separately and concomitantly in healthy Ugandan adults: a phase 1b, randomised, double-blind, placebo-controlled clinical trial," Lancet, 2015, 385:1545-1554, 10 pgs.

Ledgerwood, J.E., et al., "Chimpanzee Adenovirus Vector Ebola Vaccine—Preliminary Report," N Engl J Med, Nov. 2014, 60 pgs.

Ledgerwood, J.E., et al., "Chimpanzee Adenovirus Vector Ebola Vaccine," N Engl J Med, 2017, 376(10):928-938, 11 pgs.

Messaoudi, I., et al., "Filovirus pathogenesis and immune evasion: insights from Ebola virus and Marburg virus," Nat Rev Microbiol, Nov. 2015, 13(11):663-676, 30 pgs.

Rampling, T., et al., "A Monovalent Chimpanzee Adenovirus Ebola Vaccine—Preliminary Report," N Engl J Med, Jan. 2015, 10 pgs.

Singh, K., et al., "A novel Ebola virus antibody-dependent cell-mediated cytotoxicity (Ebola ADCC) Assay," Journal of Immunological Methods, 2018, 460:10-16, 7 pgs.

Stanley, D.A., et al., "Chimpanzee adenovirus vaccine generates acute and durable protective immunity against ebolavirus challenge," Nature Medicine, 2014, 20(10):1126-1129, 6 pgs.

Tapia, M.D., et al., "Use of ChAd3-EBO-Z Ebola virus vaccine in Malian and US adults, and boosting of Malian adults with MVA-BN-Filo: a phase 1, single-blind, randomised trial, a phase 1b, open-label and double-blind, dose-escalation trial, and a nested, randomised, double-blind, placebo-controlled trial," Lancet Infect Dis, 2016, 16(1):31-42, 12 pgs.

Warfield, K.L., et al., "Ebola Virus-Like Particle-Based Vaccine Protects Nonhuman Primates against Lethal Ebola Virus Challenge," The Journal of Infectious Diseases, 2007, 196(Suppl 2):S430-437, 8 pgs.

Warfield, K.L., et al., "Homologous and Heterologous Protection of Nonhuman Primates by Ebola and Sudan Virus-Like Particles," PloS One, 2015, 10(3):e0118881, 16 pgs.

Zhu, F-C., et al., "Safety and immunogenicity of a novel recombinant adenovirus type-5 vector-based Ebola vaccine in healthy adults in China: preliminary report of a randomised, double-blind, placebo-controlled, phase 1 trial," Lancet, 2015, 385:2272-2279, 8 pgs.

International Search Report and Written Opinion dated Jun. 14, 2018 for Application No. PCT/US2018/024747, 14 pgs.

International Search Report and Written Opinion dated Aug. 28, 2018 for Application No. PCT/US2018/024758, 11 pgs.

European Search Report, Extended, and Written Opinion dated Dec. 16, 2020 for Application No. EP 18776312.3, 25 pgs.

European Search Report, Extended, and Written Opinion dated Dec. 16, 2020 for Application No. EP 18778205.7, 24 pgs.

Kushnir, N., et al., "Virus-like particles as a highly efficient vaccine platform: Diversity of targets and production systems and advances in clinical development," Vaccine, 2012, 31:58-83, 26 pgs. XP055163741.

Hammonds, J., et al., "Gp120 stability on HIV-1 virions and Gag-Env pseudovirions is enhanced by an uncleaved Gag core," Virol, 2003, 314:636-649, 14 pgs.

Singh, K., et al., "A Bivalent, Spherical Virus-Like Particle Vaccine Enhances Breadth of Immune Responses against Pathogenic Ebola Viruses in Rhesus Macaques," J Virol, 2020, 94(9):e01884-19, 19 pgs.

Tariq, H., et al., "Virus-Like Particles: Revolutionary Platforms for Developing Vaccines Against Emerging Infectious Diseases," Front Microbiol, Jan. 2022, 12:790121, 20 pgs.

* cited by examiner

(A) EBOVGPGag VLPs (B) SUDVGPGag VLPs

FIG. 4

(A) EBOVGPGag VLP — EBOV GP, HIV-1 Gag Core (B) SUDVGPGag VLPs — SUDV GP, HIV-1 Gag Core

VLP-BASED MONOVALENT EBOLA VACCINES AND METHODS OF MAKING AND USING SAME

CROSS-REFERENCE TO RELATED APPLICATIONS

This application claims priority to and benefit of International Application No. PCT/US18/24758, entitled "VLP-Based Monovalent Ebola Vaccines and Methods of Making and Using Same" filed Mar. 28, 2018, which claims priority to and benefit of 62/477,480, entitled "Development and Evaluation of a Novel Bivalent Virus Like Particle (VLP) based Ebola Vaccine" filed Mar. 28, 2017, the contents of which are incorporated in their entirety for all purposes.

BACKGROUND

Ebolaviruses have caused epidemics in humans that are characterized by high mortality rates. The 2013-2016 Ebolavirus epidemic in West Africa resulted in more than 28,600 infections and 11,300 deaths (WHO June 2016). The extent of the outbreak coupled with a high rate of mortality emphasized the importance of developing new therapeutics and preventive vaccines against Ebolaviruses. Several candidate Ebola vaccines have shown protection in the non-human primate (NHP) model of Ebola. Three of the most promising live attenuated vaccines for Ebola are those derived from Vesicular stomatitis virus (VSV), Chimp Adenovirus Type 3 (ChAd3), and Modified Vaccinia Ankara (MVA). However, none of these approaches has proven capable of eliciting long-lasting protective immune responses.

Successful development of a vaccine will significantly help in the prevention and control of Ebola epidemics in Africa as well as protect health-care workers and researchers working with these deadly viruses. Such a vaccine will also be extremely useful in the event of a bio-terrorism attack and protecting American troops abroad. Clinical care of Ebola infected patients needs special infrastructure, restricted-access facilities and highly trained health-care workers and there is a very high cost associated with this. Thus, the economic impact of developing such a vaccine also cannot be underestimated. The instant disclosure addresses one or more of the aforementioned needs in the art.

BRIEF SUMMARY

Disclosed herein are virus-like particle (VLP)-based monovalent vaccine compositions. The compositions may comprise a spherical retroviral Group-specific Antigen ("Gag") protein core and a single Ebola glycoprotein selected from either a Zaire (EBOV) glycoprotein or a Sudan (SUDV) glycoprotein. The Ebola glycoprotein may be incorporated into the surface of the spherical Gag core, wherein said VLP-based vaccine presents a single Ebola glycoprotein antigen.

BRIEF DESCRIPTION OF THE DRAWINGS

Those of skill in the art will understand that the drawings, described below, are for illustrative purposes only. The drawings are not intended to limit the scope of the present teachings in any way.

FIG. 2. Dox induced secretion of monovalent EBOVGP-Gag or SUDVGPGag VLPs by stably transfected 293F cells. Supernatant from cells induced with Dox was layered on 20% sucrose cushion and subjected to ultracentrifugation. VLP pellets so obtained and the cell lysates were probed by western blotting using anti-EBOV GP and anti-HIV-1 Gag (A) or anti-SUDV GP and anti-HIV-1 Gag (B) specific antibodies.

FIG. 3. Buoyance density analysis of monovalent EBOVGPGag and SUDVGPGag VLPs. Fractions collected after ultracentrifugation of monovalent Ebola VLPs over 20-60% sucrose gradient were probed by western blotting using anti-EBOV GP and anti-HIV-1 Gag (A) or anti-SUDV GP and anti-HIV-1 Gag (B) specific antibodies. Buoyance density of each fraction was determined by using a refractometer.

FIG. 4. Negative electron microscopy of monovalent EBOVGPGag and SUDVGPGag VLPs. Ebola VLPs harvested from culture supernatants after ultracentrifugation on 20% sucrose cushion were analyzed by negative electron microscopy. The analysis showed spherical particles abundantly covered with spikes of glycoproteins on their surface.

FIG. 5 Immunoreactivity of rabbit anti-monovalent Ebola VLP sera with recombinant Ebola glycoproteins. Elisa plates were coated with 20 ng/well of either recombinant EBOV GP (A) or SUDV GP (B) proteins, blocked and incubated with increasing dilutions of rabbit anti-monovalent Ebola VLP sera. Protein bound antibodies were detected by incubating the wells with horse radish peroxidase (HRP) bound anti-rabbit IgG detecting antibodies followed by the addition of HRP substrate and measuring the optical density at 450 nm.

FIG. 6. Rabbit anti-monovalent Ebola VLP sera strongly neutralize all four species of Ebolavirus pathogenic to humans. EBOV, SUDV, BDBV and TAFV GP containing HIV-1ΔEnv pseudovirions were incubated with different dilutions of rabbit anti-ESGPGag VLP sera for one hour and then added onto TZM-bl cells that express luciferase under the control of HIV-1 Tat. 48 hours later luciferase activity was measured and percentage neutralization calculated by comparing luciferase activity in the test wells to that in the wells that received respective pseudovirions that was not incubated with any antibody/serum.

DETAILED DESCRIPTION

Definitions

Figure 1:
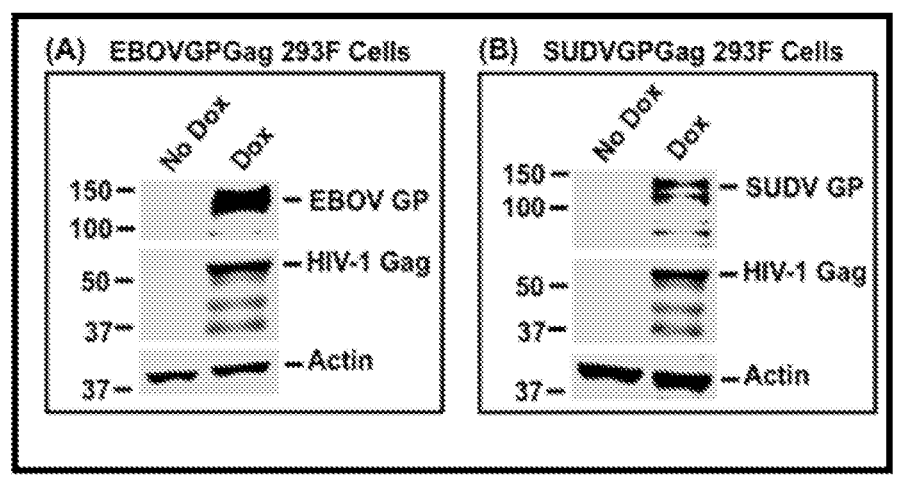
FIG. 1. Inducible expression of Ebola GPs and HIV-1 Gag in EBOVGPGag and SUDVGPGag 293F cells. (A) EBOVGPGag 293F cells and (B) SUDVGPGag 293F cells were cultured as such or induced with Dox for 24 h and cell lysates probed by western blotting for EBOV GP, HIV-1 Gag and actin (A) or SUDV GP, HIV-1 Gag and actin (B) using specific antibodies.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

Ebola virus disease (EVD) is caused by Ebola viruses that are filamentous, negative-strand RNA viruses belonging to the family Filoviridae. There are five species of the Ebola viruses; Zaire ebolavirus (EBOV), Sudan ebolavirus (SUDV), Bundibugiyo ebolavirus (BDBV), Tai-forest ebolavirus (TAFV) and Reston ebolavirus (RESTV). First four have been shown to be pathogenic in humans whereas RESTV has been shown to cause disease only in non-human primates. Ebolavirus structure consists of an inner nucleocapsid made up of nucleoprotein (NP) and containing the viral RNA, along with RNA polymerase L, transcription factor VP30 and cofactor VP35. The viral nucleocapsid is surrounded by a lipid bilayer that contains the envelope protein spikes of glycoprotein (GP). Between the viral envelope and nucleocapsid are the matrix proteins VP40 and VP24 (1). Because of its integral role in the pathogenesis of EVD, GP has been the relevant target of all the candidate Ebola vaccines developed so far.

A number of candidate Ebola vaccines have been developed and evaluated in non-human primate (NHP) model of EVD as well as in clinical trials (2-11). A few of them were fast tracked to the clinical trials during the 2013-2016 Ebola epidemic. Ebola vaccines such as the vesicular stomatitis virus (VSV), adenovirus 5 (Ad5) or chimpanzee adenovirus 3 (ChAd3)-vectored vaccines appear quite promising in generating protective immune responses. However, each candidate has substantial limitations. For example, the VSV vaccine elicits a high rate of adverse events so that acceptability for licensure remains in doubt (2, 3) Recombinant human adenoviral vectored vaccines are limited by pre-existing immunity to the vector in the human populations at risk for Ebola (4). Chimpanzee adenovirus based Ebola vaccine like ChAd3-EBO and ChAd3-EBO-Z have been developed to bypass the pre-existing immunity to the vector in the humans. However, in non-human primate models of Ebola virus disease (EVD), these vaccines did not induce durable protective immunity (11). Boosting of animals after priming with this vaccine with Modified Vaccinia Ankara (MVA)-Filo vaccine that has glycoproteins (GP) from Zaire (EBOV), Sudan (SUDV) and Marburg (MARV) viruses and nucleoprotein from Tai-Forest (TAFV) virus has been shown to extend the duration of protective immune responses against lethal EBOV challenge (11). Together these studies clearly suggested that novel Ebola vaccines, that either alone or in combination with other vaccines, are needed that can provide long-term protective immunity against the dreadful Ebolaviruses.

Disclosed herein is the successful development and production of novel virus-like particle (VLP) based monovalent Ebola vaccines that express Ebola glycoproteins (GP) from either Zaire (EBOV) or Sudan (SUDV) species on the HIV-1 Gag core. The immunogenicity of these glycoprotein VLP Ebola vaccines and their ability to generate high titers of functional neutralizing antibodies can be tested by immunizing rabbits with these vaccines combined with adjuvants Poly (I:C) and CpG. Immunization of rabbits with EBOVGPGag VLPs produced high tittered binding antibodies that neutralized all four pathogenic species of Ebola but to different degrees while immunization with SUDVGPGag VLPs produced binding antibodies that neutralized only SUDV.

The disclosed VLP platforms may be used for large-scale production of nanoparticle monovalent Ebola vaccines. The production systems may employ stable and inducible cell lines such as the EBOVGPGag 293F or SUDVGPGag cells that, upon induction with doxycycline (Dox), secret VLPs with HIV-1 Gag core abundantly studded with Ebola glycoproteins (GPs) from either Zaire (EBOV) or Sudan (SUDV) Ebolaviruses. There are several unique aspects of this VLP approach. (1) The Gag core provides a very stable framework of ~110 nm on which Ebola GPs may be incorporated in their native conformation. These stable cell production systems can be easily scaled up to produce large quantities of clinical grade Ebola VLPs. (2) The spherical Gag core exhibits enhanced stability as compared with other framework constructs such as Ebola VP40 protein. (3) The VLP-based vaccines are non-infectious, have antigen in stable and native conformation, and do not suffer from the limitation of pre-existing immunity. This Ebola vaccine may provide protection as a stand-alone vaccine, or may be even more advantageous when provided as a booster vaccine following priming with other experimental Ebola vaccines.

Disclosed herein are virus-like particle (VLP)-based monovalent vaccine compositions. The compositions may comprise a spherical retroviral Group-specific Antigen ("Gag") protein core and a single Ebola glycoprotein selected from either a Zaire (EBOV) glycoprotein or a Sudan (SUDV) glycoprotein. SUDV is described as YP_138523.1 in the literature, whereas an example of EBOV GP is reported as NCBI Reference Sequence: NP_066246.1, both incorporated herein in their entirety by reference. The Ebola glycoprotein may be incorporated into the surface of the spherical Gag core, wherein said VLP-based vaccine presents a single Ebola glycoprotein antigen. An exemplary Gag protein includes, but is not limited to, that of SEQ ID NO: 1. Exemplary glycoproteins include, but are not limited to, those set forth in SEQ ID NOS 2, 3, and 4. It will be understood by one of ordinary skill in the art that one may employ a sequence having at least 50%, 60%, 70%, 75%, 80%, 85%, 90%, 95%, 96%, 97%, 98%, 99%, or 100% identity to the reference sequence, which may include the sequences disclosed herein or as otherwise known in the art. The length of comparison sequences may be at least 5 contiguous nucleotides or amino acids, or at least 10, 11, 12, 13, 14, 15, 16, 17, 18, 19, 20, 21, 22, 23, 24, or 25 contiguous nucleotides or amino acids, or the full-length nucleotide or amino acid sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

In one aspect, the Gag protein may be derived from a retrovirus. For example, suitable retroviruses from which the gag protein may be derived include human immunodeficiency virus (HIV), murine leukemia virus (MLV) Rous sarcoma virus (RSV), Equine infectious anemia virus (EIAV), or the like. The sequences of such will be readily appreciated by one of ordinary skill in the art.

In one aspect, it has been surprisingly found that the glycoprotein is capable of aggregating at a relatively high density at the surface of the spherical gag core. In certain aspects, the EBOV GP Concentration may be about 20 to about 200 ug/mL, or about 40 to about 150, or about 80 to 100 ug/ml, for example in one aspect, 23 to 184 ug/ml. The SUDV GP Concentration may be about 10 to about 60 ug/ml, or about 20 to about 50 ug/mL, or about 30 to about 40 ug/ml, for example, in one aspect, 13-53 ug/ml. The HIV-1 Gag Concentration may be about 1 to about 10 ug/ml, or about 3 to about 10 ug/ml. The concentrations of EBOV GP and SUDV GP, may be measured by semi-quantitative western blotting using known quantities of purified recombinant EBOV GP and SUDV GP respectively. Concentrations of HIV-1 Gag VLPs may be measured by an HIV-1 Gag specific ELISA using known quantities of purified HIV-1 Gag. In one aspect, the spherical Gag protein core may have a diameter of from about 100 to about 300 nanometers or about 200 to about 250 nanometers.

In one aspect, the VLP composition may be sufficient to immunize an individual against a viral infection from one or more of Zaire (EBOV), Sudan (SUDV), Bundibugyo (BDBV) and Tai Forest (TAFV), or in some aspects, two or more of Zaire (EBOV), Sudan (SUDV), Bundibugyo (BDBV) and Tai Forest (TAFV), or three or more of Zaire (EBOV), Sudan (SUDV), Bundibugyo (BDBV) and Tai Forest (TAFV), or all four of Zaire (EBOV), Sudan (SUDV), Bundibugyo (BDBV) and Tai Forest (TAFV).

The disclosed compositions may further comprise one or more pharmaceutical-acceptable carriers, which may include any and all solvents, dispersion media, coatings, stabilizing agents, diluents, preservatives, antibacterial and antifungal agents, isotonic agents, adsorption delaying agents, and the like. The disclosed S particles may be provided in physiological saline. Optionally, a protectant may be included, for example, an anti-microbiological active agent, such as for example Gentamycin, Merthiolate, and the like. The compositions may further include a stabilizing agent, such as for example saccharides, trehalose, mannitol, saccharose and the like, to increase and/or maintain product shelf-life. Those of skill in the art will understand that the composition herein may incorporate known injectable, physiologically acceptable sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants will be appreciated by one of ordinary skill in the art.

In one aspect, disclosed is a container comprising at least one dose of the immunogenic compositions disclosed herein. The container may comprise 1 to 250 doses of the immunogenic composition, or in other aspects, 1, 10, 25, 50, 100, 150, 200, or 250 doses of the immunogenic composition. In one aspect, each of the containers may comprise more than one dose of the immunogenic composition and may further comprises an anti-microbiological active agent. Those agents may include, for example, antibiotics such as Gentamicin and Merthiolate and the like.

A further aspect relates to a kit. The kit may comprise any of the containers described above and an instruction manual, including the information for the delivery of the immunogenic composition disclosed above. For example, instructions related to intramuscular application of at least one dose may be provided for lessening the severity of clinical symptoms associated with an infection of an antigen as disclosed here. The kits and/or compositions may further include an immune stimulant such as keyhole limpet hemocyanin (KLH), or incomplete Freund's adjuvant (KLH/ICFA). Any other immune stimulant known to a person skilled in the art may also be used.

In one aspect, a method for eliciting an immune response an individual in need thereof against an Ebola virus species selected from Zaire (EBOV), Sudan (SUDV), Bundibugyo (BDBV), Tai Forest (TAFV), and combinations thereof is disclosed. The method may comprise the step of administering a composition as disclosed herein. In this aspect, the method may include the step of administering a vaccine composition as disclosed above to an individual in need thereof. It will be readily appreciated that the disclosed compositions may be administered to an individual according to any method known in the art, and that optimal administration (including route and amounts) will not require undue experimentation. The vaccine compositions may be administered prophylactically to an individual suspected of having a future exposure to the antigen incorporated into the vaccine composition. In certain aspects, provided is a method of providing an immune response that protects an individual receiving the composition from infection, or reduces or lessens the severity of the clinical symptoms associated from an Ebola infection. Dosage regimen may be a single dose schedule or a multiple dose schedule (e.g., including booster doses) with a unit dosage form of the composition administered at different times. The term "unit dosage form," as used herein, refers to physically discrete units suitable as unitary dosages for human and animal subjects, each unit containing a predetermined quantity of the antigenic compositions disclosed herein in an amount sufficient to produce the desired effect, which compositions are provided in association with a pharmaceutically acceptable excipient (e.g., pharmaceutically acceptable diluent, carrier or vehicle). The vaccine may be administered in conjunction with other immunoregulatory agents.

The dosage regimen may take a variety of different forms. For example, the individual may be administered a first dose of the disclosed composition followed by a second dose of the composition. In certain aspects, the second dose may be administered at a second point in time selected from a day after the first dose, a week after the first dose, two weeks after the first dose, three weeks after the first dose, and four weeks after the first dose.

In one aspect, a method of making the monovalent VLP compositions is disclosed. The method may comprise the steps of purifying from a cell line a VLP composition comprising a spherical retroviral Group-specific Antigen ("Gag") protein core and an Ebola glycoprotein, wherein the Ebola glycoprotein may be incorporated into the surface of the spherical Gag protein core. The cell line may be stably transfected with a first plasmid containing a gag sequence under the control of an inducible promoter and a second plasmid containing an Ebola glycoprotein sequence under the control of an inducible promoter. The stably transfected cell line may produce the spherical Gag protein core such that the Ebola glycoprotein is located at the surface of the spherical Gag protein core. The stably transfected cell line may be such that the Gag protein core is produced upon induction with doxycycline. The first and second plasmid may be antibiotic resistant. This antibiotic resistance allows the cells stably transfected with the two plasmids to grow in a selection media containing the two antibiotics. The VLP may then be purified by ultracentrifugation, such as via a sucrose cushion, for example, a 20% sucrose cushion, or by cross-flow filtration followed by ultracentrifugation.

In one aspect, the cell line may be a human cell line modified to stably express Gag, EBOV GP or SUDV GP under inducible promoters. In one aspect, the cell line may be a 293F cell line, in a further aspect, the cell line may be a 293F 6/TR cell line In one aspect, a cell line comprising a first plasmid containing a sequence encoding for a gag protein under the control of an inducible promoter, and a second plasmid containing a sequence encoding for an Ebola glycoprotein under the control of an inducible promoter is disclosed. The Ebola glycoprotein may be one of EBOV or SUDV. In one aspect, the cell line may be a 293F cell line, in a further aspect, the cell line may be a 293F 6/TR cell line the cell line may be stably transfected with the plasmids. In certain aspects, the cell line may be an inducible cell line. Any of the aforementioned sequences may be codon-optimized. Codon optimization is readily understood by one of ordinary skill in the art, described, for example, at https://www.idtdna.com/CodonOpt.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Methods

Plasmids: Plasmids useful for the disclosed methods compositions are described as follows. The HIV-1 Gag gene was introduced between HindIII and BamHI sites of plasmid pcDNA4/TO (Invitrogen, Carlsbad, CA) to generate plasmid pcDNA4/TO HIV-1 Gag. pcDNA5/TO-puro and pcDNA5/TO-puro plasmids may be created by replacing hygromycin resistance gene sequence of original pcDNA5/TO vector (Invitrogen, Carlsbad, CA) with a puromycin resistance gene. Briefly, the puromycin resistance gene was amplified by polymerase chain reaction (PCR). The hygromycin resistance gene was deleted from the original pcDNA5/TO plasmid by digestion with enzyme Pml I, and the puromycin resistance gene inserted in its place. The sequence and orientation of the inserts may be verified. Codon-optimized EBOV GP Mayinga gene may be synthesized by GenScript (Piscataway, NJ) and placed under a tetracycline-controlled cytomegalovirus (CMV) promoter into plasmid pcDNA5/TO-puro using BamHI and EcoRI sites to generate the plasmid pcDNA5/TO-puro EBOV GP. Codon-optimized SUDV GP Gulu gene may be purchased from Sino-Biological (Beijing, China) and placed under a tetracycline-controlled cytomegalovirus (CMV) promoter into plasmid pcDNA5/TO-puro using HindIII and XbaI sites to generate the plasmid pcDNA5/TO-puro SUDV GP.

Stably transfected EBOVGPGag 293F and SUDVGPGag 293F cells with inducible expression of EBOV GP, or SUDV GP and HIV-1 Gag: 293F cells, cultured in 293 Expression Media supplemented with 5 µg/ml blasticidin (Invivogen, San Diego, CA), may be transfected with pcDNA4/TO HIV-1 Gag and pcDNA5/TO-puro EBOV GP or with pcDNA4/TO HIV-1 Gag and pcDNA5/TO-puro SUDV GP plasmids together using Lipofectamine 2000. Forty-eight hours later, the cells may be washed and transferred into the selection media (293 Expression Media supplemented with 5 µg/ml blasticidin, 10 µg/ml Zeocin (Invivogen) and 1.0 µg/ml puromycin (Invivogen)). Cells may be selected and expanded over the coming weeks till their number reached ~10~$10^6$. A part of the cells may be harvested and aliquots may be cryopreserved in liquid nitrogen. Remaining cells may be continued in the cultured and then either left untreated or induced with Dox (2 µg/ml) (Sigma-Aldrich) for 24 hours, cells harvested and cell lysates tested for EBOV GP or SUDV GP and HIV-1 Gag expression by western blotting using specific antibodies. Cell cultures with high EBOV GP or SUDV GP and HIV-1 Gag expression may be selected and labeled EBOVGPGag and SUDVGPGag 293F cells respectively, expanded and selected for further work. Multiple aliquots of these cells may be cryopreserved in liquid nitrogen.

Analysis of EBOVGPGag and SUDVGPGag VLPs Secreted by 293F Cells Stably Transfected With Ebola GPs EBOVGPGag and SUDVGPGag 293F cells may be cultured in 293 Expression Media in Erlenmeyer flasks to a density of $1.5 \times 10^6$ cells per ml and cultures induced with Dox (2 µg/ml). 40 hours later, cells and supernatants may be separated by high-speed centrifugation. Harvested cells may be lysed and cell lysates frozen in −80° C. freezer. The supernatant was cleared by centrifugation and by passing through 0.45 micron filtration unit. Cleared supernatant was loaded on a 20% sucrose cushion in ultracentrifuge tubes and tubes centrifuged at 30,000 rpm for 90 minutes at 4oC in a Beckman Coulter Optima XPN90 ultracentrifuge. VLP pellets may be re-suspended in PBS. Cell lysates and VLPs may be resolved on 10% polyacrylamide gels, proteins transferred onto nitrocellulose membranes and the membranes probed by western blotting for the presence EBOV GP, or SUDV GP and HIV-1 Gag using specific antibodies.

Production and Characterization of EBOVGPGag and SUDVGPGag VLPs

Once confirmed for EBOVGPGag or SUDVGPGag VLP secretion, stably transfected 293F cell cultures may be scaled up, VLP pellets may be collected as described above and layered on a 20-60% sucrose gradient in ultracentrifuge tubes. Tubes may be centrifuged at 35,000 rpm at 4° C. for 16 hours in an ultracentrifuge. After discarding the top 1.0 ml, twelve 900 µl fractions may be collected in clean tubes. Buoyance density of each fraction may be determined by using a refractometer. Fractions may be probed by western blotting using anti-EBOV GP, or anti-SUDV GP and anti-HIV-1 Gag specific antibodies. In separate experiments, VLPs collected after centrifugation on 20% sucrose cushion may be analyzed by negative-stain electron microscopy for their shape and size. VLPs from multiple runs may be pooled and quantified for EBOV GP or SUDV GP contents by quantitative western blotting using known amounts of recombinant EBOV GP protein or SUDV GP protein as the standards and specific antibodies.

Immunization of Rabbits With EBOVGPGag or SUDVGPGag VLPs

Raising of rabbit sera against EBOVGPGag or SUDVGP-Gag VLPs may be out-sourced to Cocalico Biologicals, Reamstown, PA Briefly, two rabbits may be primed intramuscularly with VLPs (equivalent to 10 ug of either of the two Ebola GP) mixed with 500 ug of CpG and 200 ug of Poly(I:C) adjuvants. This may be followed by booster doses on day 21, 42 and 70 and animals may be bled on day 77. Blood samples for serum may be collected at pre-bleed and at days 49 and 77.

Binding Antibodies

ELISA binding antibody titers against EBOV GP or SUDV GP may be quantified by ELISA using purified recombinant GPs as the coating antigens. Briefly, ELISA plates may be coated with 100 ul/well of 200 ng/ml of recombinant EBOV GP or SUDV GP. Wells may be blocked and incubated for 2 hours at 37° C. with increasing dilutions of rabbit anti-EBOVGPGag or SUDVGPGag VLP sera. Protein bound antibodies may be detected by incubating the wells with optimally diluted horse radish peroxidase (HRP) bound anti-rabbit IgG detecting antibodies followed by the addition of TMB substrate, stopping the reaction with $H_2SO_4$ and measuring the optical density at 450 nm.

Neutralizing Antibody Titers

Neutralizing antibody titers may be evaluated by using rHIV-1ΔEnv pseudovirions expressing EBOV or SUDV GP in a TZM-bl pseudovirus reporter cell method. rHIV-1ΔEnv pseudovirions expressing BDBV or TAFV GP may be included to study the ability of anti-ESGPGag VLP sera to cross-neutralize other pathogenic Ebolaviruses as well as MARV. Pseudovirions may be incubated with different dilutions of rabbit anti-EBOVGPGag or SUDVGPGag VLP sera for one hour at 37oC and then added onto confluent TZM-bl cells that express luciferase under the control of an HIV-1 Tat protein. 48 hours later luciferase activity may be measured after the addition of the luciferase substrate and percentage neutralization calculated by comparing luciferase number in test wells with those in the wells that received the respective pseudovirion that was not incubated with any antibody/serum. Serum antibody titers giving 50% neutralization may be calculated.

Results and Discussion

Development of Stably Transfected 293F Cells Producing Monovalent Ebola VLPs

Figure 2:
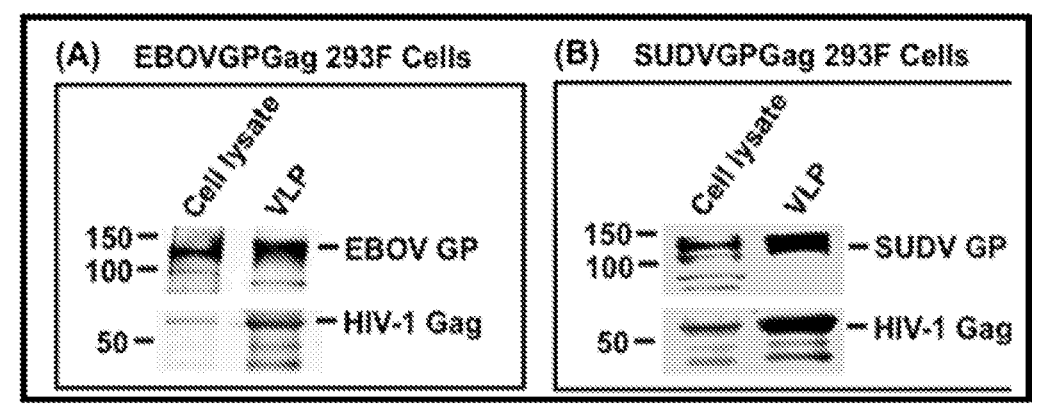

Transfection of 293F with pcDNA4 TO-HIV-1 Gag and pcDNA5 TO-EBOV GP or pcDNA4 TO-HIV-1 Gag and pcDNA5 TO-SUDV GP plasmids followed by their selection in antibiotic containing media over a four-week period resulted in the development of cells that upon induction with Dox produced HIV-1 Gag and EBOV GP or SUDV GP respectively (FIGS. 1A and 1B) indicating that these gene pairs have been stably integrated into the genome of these cells and can be turned on with the addition of Dox. Applicant labeled these stably transfected cells as EBOVGPGag 293F cells or SUDVGPGag 293F cells respectively. Experiments may be conducted to determine if EBOV GP and HIV-1 Gag or SUDV GP and HIV-1 Gag synthesized in these cells, after Dox induction, could spontaneously assemble into VLPs and be secreted into the medium. VLPs may be isolated from the cell supernatant collected after 40 hours of Dox induction and may be analyzed, along with the corresponding cell lysates, by western blotting for the presence either EBOV GP or SUDV GP along with HIV-1 Gag proteins using specific antibodies. As shown in FIG. 2, full length EBOV GP (2A) or SUDV GP (2B) and HIV-1 Gag may be detected in the cell lysate and in the VLPs indicating that either of the two Ebola GPs and HIV-1 Gag, synthesized upon induction of stably transfected 293F cells with Dox spontaneously assemble into VLPs that are secreted out into the medium.

Characterization of Monovalent Ebola VLPs

Figure 3:
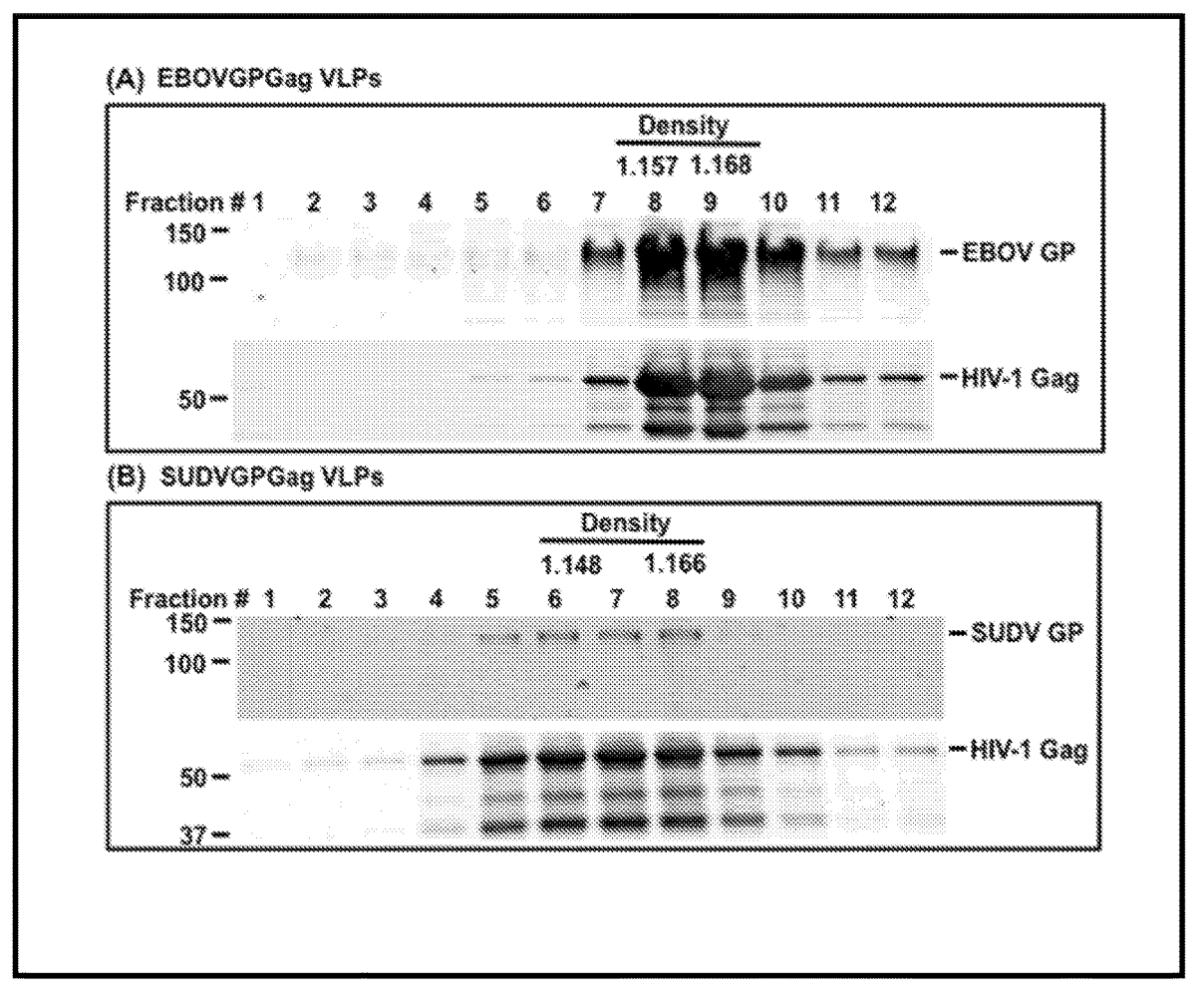

Buoyance density analysis of monovalent Ebola VLP fractions collected over 20-60% sucrose density gradient showed that these particles range in density from 1.148-1.168 (FIG. 3). Electron microscopic analysis of the particles showed fine, spherical particles with a size of ~110 nm with EBOV GP or SUDV GP abundantly studded on the Gag matrix (FIG. 4A and B). The particle density, shape and size observed in this study is in agreement with other VLPs and immature HIV-1 virions where Gag constitutes the spherical immature shell.

Figure 5:
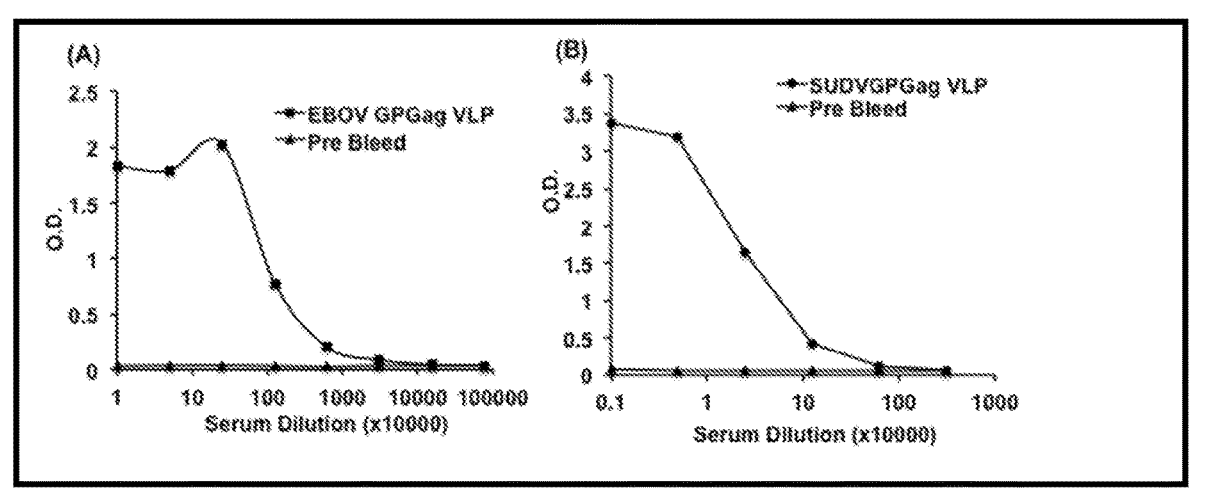
Figure 6:
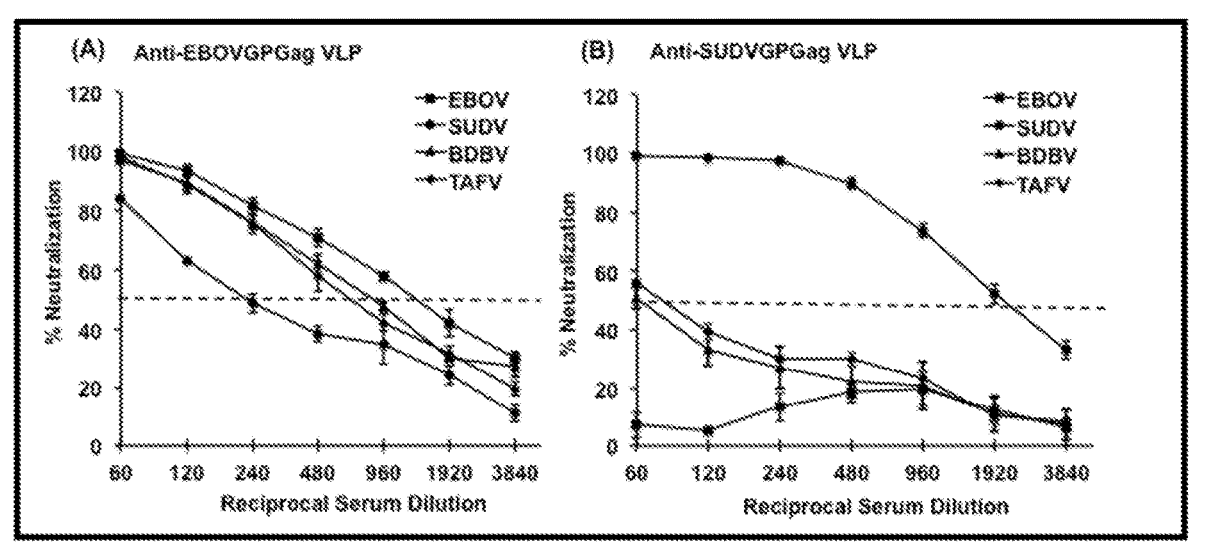

Immunogenicity of monovalent Ebola VLPs: Immunogenicity of monovalent Ebola VLPs may be tested by their ability to induce high-titered binding anti-EBOV GP or SUDV GP antibody responses in rabbits. Rabbit serum samples collected one week after the last booster dose may be heat inactivated and binding titers determined by analyzing the binding of antibodies present in increasing dilutions of the anti-sera to either EBOV GP or SUDV GP coated ELISA plates. As shown in FIGS. 5A and 5B, monovalent Ebola VLPs may be highly immunogenic in rabbits and anti-sera collected had anti-EBOV GP or SUDV GP end point antibody titers approaching $10^7$ and $10^6$ respectively. Specificity of these antibodies may be confirmed by their reactivity with recombinant EBOV GP or SUDV GP in a western blot system (data not shown). Functionality of these serum antibodies may be investigated by their ability to neutralize EBOV GP or SUDV GP containing HIV-1ΔEnv pseudovirions in a luciferase based neutralization assay using TZM-bl cells. Luciferase gene in these cells is under the control of HIV-1 Tat protein. Additionally, BDBV GP, or TAF GP containing HIV-1ΔEnv pseudovirions may be included in these assays to study the ability of either of the two anti-Ebola VLP sera to cross-neutralize other pathogenic members of this species. FIG. 6 summarizes the results of neutralization experiments using these two kinds of sera. Anti-EBOVGPGag VLP serum strongly neutralized EBOV with 50% neutralization titers of >1:960 while that against BDBV and TAFV >1:480. 50% neutralization titer for SUDV was significantly lower (1:120) (FIG. 6A). Anti-SUDVGPGag VLP serum neutralized only SUDV with 50% neutralization titers >1:1920 while no significant neutralization was observed against EBOV, BDBV and TAFV (FIG. 6B).

Ebola VLP-based vaccine on Ebola VP40 core has been used in the past to immunize non-human primates that were subsequently challenged with lethal doses of Ebola virus. This vaccine induced humoral and cellular immune responses in animals that protected these animals against the Ebola challenge (12, 13). Because of the filamentous nature of the VP40 core, these VLPs were found to be unstable. Moreover, they were produced after the transient transfection of the cells and therefore are not readily amenable to large-scale production. The disclosed VLPs are produced, in an inducible fashion, from the stably transfected 293F cells. This production system may be easily adapted to large scale Ebola VLPs production, if needed. Being smaller in size and spherical in shape they are likely to be a stable and homogenous product.

REFERENCES

1. Messaoudi I, Amarasinghe G K, Basler C F. Filovirus pathogenesis and immune evasion: insights from Ebola virus and Marburg virus. Nat Rev Microbiol. 2015; 13(11):663-76.
2. Agnandji S T, Huttner A, Zinser M E, Njuguna P, Dahlke C, Fernandes J F, et al. Phase 1 Trials of rVSV Ebola Vaccine in Africa and Europe—Preliminary Report. N Engl J Med. 2015.
3. Huttner A, Dayer J A, Yerly S, Combescure C, Auderset F, Desmeules J, et al. The effect of dose on the safety and immunogenicity of the VSV Ebola candidate vaccine: a randomised double-blind, placebo-controlled phase 1/2 trial. Lancet Infect Dis. 2015; 15(10):1156-66.
4. Ledgerwood J E, DeZure A D, Stanley D A, Novik L, Enama M E, Berkowitz N M, et al. Chimpanzee Adenovirus Vector Ebola Vaccine—Preliminary Report. N Engl J Med. 2014.
5. Kibuuka H, Berkowitz N M, Millard M, Enama M E, Tindikahwa A, Sekiziyivu A B, et al. Safety and immunogenicity of Ebola virus and Marburg virus glycoprotein DNA vaccines assessed separately and concomitantly in healthy Ugandan adults: a phase 1b, randomised, double-blind, placebo-controlled clinical trial. Lancet. 2015; 385 (9977):1545-54.
6. Rampling T, Ewer K, Bowyer G, Wright D, Imoukhuede E B, Payne R, et al. A Monovalent Chimpanzee Adenovirus Ebola Vaccine—Preliminary Report. N Engl J Med. 2015.
7. Tapia M D, Sow S O, Lyke K E, Haidara F C, Diallo F, Doumbia M, et al. Use of ChAd3-EBO-Z Ebola virus vaccine in Malian and US adults, and boosting of Malian adults with MVA-BN-Filo: a phase 1, single-blind, randomised trial, a phase 1b, open-label and double-blind, dose-escalation trial, and a nested, randomised, double-blind, placebo-controlled trial. Lancet Infect Dis. 2016; 16(1):31-42.
8. Zhu F C, Hou L H, Li J X, Wu S P, Liu P, Zhang G R, et al. Safety and immunogenicity of a novel recombinant adenovirus type-5 vector-based Ebola vaccine in healthy adults in China: preliminary report of a randomised, double-blind, placebo-controlled, phase 1 trial. Lancet. 2015; 385(9984):2272-9.
9. Henao-Restrepo A M, Longini I M, Egger M, Dean N E, Edmunds W J, Camacho A, et al. Efficacy and effectiveness of an rVSV-vectored vaccine expressing Ebola surface glycoprotein: interim results from the Guinea ring vaccination cluster-randomised trial. Lancet. 2015; 386 (9996):857-66.
10. Ledgerwood J E, DeZure A D, Stanley D A, Coates E E, Novik L, Enama M E, et al. Chimpanzee Adenovirus Vector Ebola Vaccine. N Engl J Med. 2017; 376(10):928-38.
11. Stanley D A, Honko A N, Asiedu C, Trefry J C, Lau-Kilby A W, Johnson J C, et al. Chimpanzee adenovirus vaccine generates acute and durable protective immunity against ebolavirus challenge. Nature medicine. 2014; 20(10):1126-9.
12. Warfield K L, Dye J M, Wells J B, Unfer R C, Holtsberg F W, Shulenin S, et al. Homologous and heterologous protection of nonhuman primates by Ebola and Sudan virus-like particles. PLoS one. 2015; 10(3):e0118881.
13. Warfield K L, Swenson D L, Olinger G G, Kalina W V, Aman M J, Bavari S. Ebola virus-like particle-based vaccine protects nonhuman primates against lethal Ebola virus challenge. The Journal of infectious diseases. 2007; 196 Suppl 2:S430-7.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A virus-like particle (VLP)-based monovalent vaccine composition comprising
   a spherical retroviral Group-specific Antigen ("Gag") protein core; and
   an Ebola glycoprotein selected from either a full-length Zaire (EBOV) glycoprotein or a full-length Sudan (SUDV) glycoprotein,
   said Ebola glycoprotein being incorporated into the surface of said spherical retroviral Gag protein core in a native conformation;
   said VLP-based monovalent vaccine having an EBOV glycoprotein, said EBOV glycoprotein having a density at the surface of the spherical retroviral Gag protein core of about 20 to about 200 µg/mL or an SUDV glycoprotein, said SUDV glycoprotein having a density at the surface of the spherical retroviral Gag protein core of about 10 to about 60 µg/mL.

2. The VLP composition of claim 1, wherein said Ebola glycoprotein is located at the exterior surface of said spherical Gag protein core.

3. The VLP composition of claim 1, wherein said composition is capable of immunizing an individual against a viral infection from one or more of Zaire (EBOV), Sudan (SUDV), Bundibugyo (BDBV) and Tai Forest (TAFV).

4. The VLP composition of claim 1, wherein said spherical Gag protein core is ranges from approximately 100-300 nanometers in diameter.

5. The composition of claim 1, further comprising an adjuvant.

6. The composition of claim 1, further comprising a pharmaceutically acceptable carrier.

7. A kit comprising the composition of claim 1, wherein said composition is provided in a unit dose.

8. The kit of claim 7, further comprising a second unit dose.

9. The kit of claim 7, further comprising a delivery vehicle for said composition.

10. A method for inducing an Ebola virus (EBOV)-specific immune response in an individual in need thereof, comprising administering a first dose of the composition of claim 1.

11. The method of claim 10, wherein said individual is administered a second dose of the composition of claim 1.

12. The method of claim 11, wherein said second dose is administered at a second point in time selected from a day after the first dose, a week after the first dose, two weeks after the first dose, three weeks after the first dose, and four weeks after the first dose.

13. A method of making the monovalent VLP composition of claim 1, comprising the steps of
   a. purifying from a cell line a VLP composition comprising a spherical retroviral Group-specific Antigen ("Gag") protein core and an Ebola glycoprotein, wherein said Ebola glycoprotein is incorporated into the surface of said spherical Gag protein core;
   wherein said cell line is stably transfected with a first plasmid containing a gag sequence under the control of an inducible promoter and a second plasmid containing an Ebola glycoprotein sequence under the control of an inducible promoter.

14. The method of claim 13, wherein said stably transfected cell line produces said spherical Gag protein core, and wherein said Ebola glycoprotein is located at the surface of said spherical Gag protein core.

15. The method of claim 13, wherein said stably transfected cell line produces said Gag protein core upon induction with doxycycline.

16. The method of claim 13, wherein said VLP is purified by ultracentrifugation, wherein said purification is through a sucrose cushion.

17. The method of claim 13, wherein said first and second plasmid are antibiotic resistant.

18. The method of claim 13, wherein said cell line is a human cell line modified to stably express Gag, EBOV GP or SUDV GP under inducible promoters.

19. The method of claim 13, wherein said cell line is a 293F cell line.

20. The method of claim 13, wherein said cell line is a 293F6/TR cell line.

21. The vaccine composition of claim 1, further comprising saline.

22. The vaccine composition of claim 1, further comprising a preservative.

23. The vaccine composition of claim 1, further comprising an adjuvant.

24. The vaccine composition of claim 1, wherein said composition is sterile.

* * * * *

SEQUENCE LISTING

<160> NUMBER OF SEQ ID NOS: 4

<210> SEQ ID NO 1
<211> LENGTH: 1503
<212> TYPE: DNA
<213> ORGANISM: Artificial Sequence
<220> FEATURE:
<223> OTHER INFORMATION: Codon-optimized HIV-1 Gag sequence

<400> SEQUENCE: 1

```
atgggcgccc gcgccagcgt gctgagcggc ggcgagctgg accgctggga gaagatccgc        60
ctgcgccccg cggcaagaa gaagtacaag ctgaagcaca tcgtgtgggc cagccgcgag       120
ctggagcgct tcgccgtgaa ccccggcctg ctggagacca gcgagggctg ccgccagatc       180
ctgggccagc tgcagcccag cctgcagacc ggcagcgagg agctgcgcag cctgtacaac       240
accgtggcca ccctgtactg cgtgcaccag cgcatcgaga tcaaggacac caaggaggcc       300
ctggacaaga tcgaggagga gcagaacaag agcaagaaga aggcccagca ggccgccgcc       360
gacaccggcc acagcaacca ggtgagccag aactacccca tcgtgcagaa catccagggc       420
cagatggtgc accaggccat cagcccccgc accctgaacg cctgggtgaa ggtggtggag       480
gagaaggcct tcagccccga ggtgatcccc atgttcagcg ccctgagcga gggcgccacc       540
ccccaggacc tgaacaccat gctgaacacc gtgggcggcc accaggccgc catgcagatg       600
ctgaaggaga ccatcaacga ggaggccgcc gagtgggacc gcgtgcaccc cgtgcacgcc       660
ggccccatcg cccccggcca gatgcgcgag ccccgcggca cgacatcgc cggcaccacc       720 agcaccctgc aggagcagat cggctggatg accaacaacc cccccatccc cgtgggcgag       780
atctacaagc gctggatcat cctgggcctg aacaagatcg tgcgcatgta cagccccacc       840
agcatcctgg acatccgcca gggccccaag gagcccttcc gcgactacgt ggaccgcttc       900
tacaagaccc tgcgcgccga gcaggccagc caggaggtga agaactggat gaccgagacc       960
ctgctggtgc agaacgccaa ccccgactgc aagaccatcc tgaaggccct gggccccgcc      1020
gccaccctgg aggagatgat gaccgcctgc cagggcgtgg gcggcccgg ccacaaggcc      1080 cgcgtgctgg ccgaggccat gagccaggtg accaacagcg ccaccatcat gatgcagcgc      1140
ggcaacttcc gcaaccagcg caagatcgtg aagtgcttca ctgcggcaa ggagggccac      1200 accgcccgca actgccgcgc cccccgcaag aagggctgct ggaagtgcgg caaggagggc      1260
caccagatga aggactgcac cgagcgacag gctaatttt tagggaagat ctggccttcc      1320
cacaagggaa ggccagggaa ttttcttcag agcagaccag agccaacagc cccaccagaa      1380
gagagcttca ggtttgggga agagacaaca actccctctc agaagcagga gccgatagac      1440
aaggaactgt atcctttagc ttccctcaga tcactctttg gcagcgaccc ctcgtcacaa      1500
taa                                                                   1503
```

<210> SEQ ID NO 2
<211> LENGTH: 2035
<212> TYPE: DNA
<213> ORGANISM: Artificial Sequence
<220> FEATURE:
<223> OTHER INFORMATION: EBOV GP

<400> SEQUENCE: 2

```
atgggcgtca ctggtattct gcagctgccc cgagataggt tcaagcggac ttccttcttc      60
ctgtgggtca tcattctgtt tcagcggact ttcagcatcc ctctgggcgt gattcacaac     120
tcaaccctgc aggtgagcga cgtggataag ctggtctgtc gcgacaaact gagctccacc     180
aatcagctgc gatccgtggg actgaatctg gagggtaacg gagtggcaac tgatgtccca     240
agcgccacca acggtgggg gtttaggtcc ggtgtgcccc ctaaggtggt caactacgag      300
gctggcgaat gggcagagaa ttgctataac ctggaaatca gaaacctga cggcagcgag     360
tgtctgccag cagctcctga tggcattagg ggattcccta ggtgcagata cgtgcacaaa     420
gtctctggaa ccgggccatg tgccggagac ttcgcttttc ataaggaagg ggcattcttt     480
ctgtacgatc gactggcctc caccgtgatc tatcggggaa ccacattcgc tgaggggtg      540
gtcgcatttc tgattctgcc ccaggctaag aaagacttct tttctagtca cccactgcgc     600
gaacccgtga cgcaaccga ggaccgctca agcggctact atagtactac catccgatac     660
caggccacag gtttcggcac aaatgagact gaatacctgt ttgaagtgga caacctgact     720
tatgtccagc tggagagcag gttcacccct cagtttctgc tgcagctgaa cgaaaccatc     780
tatacaagcg gcaagcggag caatacaact ggcaagctga tttggaaagt gaacccagag     840
atcgatacca aattggcga atgggccttt tgggagacaa agaaaaatct gactcgcaaa     900
atccgatctg aggaactgag tttcaccgtg gtctccaatg gtgctaagaa cattagtggc     960
cagtcaccag cacgcacatc ctctgacccc gggactaata ctaccacaga agatcacaag    1020
atcatggcat ctgagaacag ttcagccatg gtgcaggtcc acagtcaggg acgagaggca    1080
gccgtgtcac atctgactac cctggccact atctctacca gtccacagtc tctgacaact    1140
aaacctggac cagacaatag tacacataac actcccgtgt acaagctgga tattagtgaa    1200
gccacacagg tcgagcagca ccatcggagg actgacaacg atagcaccgc ttccgacaca    1260
ccatcagcaa ccacagctgc aggcccaccc aaagctgaga ataccaacac atcaaagagc    1320
actgacttcc tggaccccgc cactaccaca tccccacaga atcactctga cacagctgga    1380
aacaataaca cccaccatca ggacacaggg gaggaatctg ccagctccgg aagctgggt    1440
ctgatcacta acaccattgc cggcgtggct ggactgatca ctggcggaag acgcacccga    1500
cgggaagcaa ttgtgaatgc ccagcctaag tgcaatccaa acctgcacta ctggactacc    1560
caggacgagg gagcagctat cggactggct tggattccct acttcgggcc tgcagccgaa    1620
ggtatctata ttgagggcct gatgcataat caggatgggc tgatctgtgg tctgcgccag    1680
ctggccaacg aaacaactca ggctctgcag ctgttcctga gcaaccacc agagctgcgc    1740
accttttcta tcctgaacag gaaggccatt gacttcctgc tgcagagatg gggaggtaca    1800
tgccacatcc tgggaccaga ctgctgtatt gagcctcatg attggactaa gaatatcacc    1860
gacaaaattg atcagatcat tcacgacttt gtggataaga cactgcctga tcagggtgac    1920
aatgataact ggtggactgg atggcgacag tggattcccg caggaattgg ggtgaccggc    1980
gtcatcattg cagtgatcgc cctgttttgc atttgtaaat tcgtgttttg agaat         2035
```

<210> SEQ ID NO 3
<211> LENGTH: 676
<212> TYPE: PRT
<213> ORGANISM: Zaire (EBOV) glycoprotein from Zaire ebolavirus

<400> SEQUENCE: 3

Met Gly Val Thr Gly Ile Leu Gln Leu Pro Arg Asp Arg Phe Lys Arg

```
            1               5                      10                    15
        Thr Ser Phe Phe Leu Trp Val Ile Ile Leu Phe Gln Arg Thr Phe Ser
                        20                      25                  30

Ile Pro Leu Gly Val Ile His Asn Ser Thr Leu Gln Val Ser Asp Val
                        35                      40                  45

Asp Lys Leu Val Cys Arg Asp Lys Leu Ser Ser Thr Asn Gln Leu Arg
                        50                      55                  60

Ser Val Gly Leu Asn Leu Glu Gly Asn Gly Val Ala Thr Asp Val Pro
         65                      70                  75                  80

Ser Ala Thr Lys Arg Trp Gly Phe Arg Ser Gly Val Pro Pro Lys Val
                        85                      90                  95

Val Asn Tyr Glu Ala Gly Glu Trp Ala Glu Asn Cys Tyr Asn Leu Glu
                        100                     105                 110

Ile Lys Lys Pro Asp Gly Ser Glu Cys Leu Pro Ala Ala Pro Asp Gly
                        115                     120                 125

Ile Arg Gly Phe Pro Arg Cys Arg Tyr Val His Lys Val Ser Gly Thr
                        130                     135                 140

Gly Pro Cys Ala Gly Asp Phe Ala Phe His Lys Glu Gly Ala Phe Phe
        145                     150                 155                 160

Leu Tyr Asp Arg Leu Ala Ser Thr Val Ile Tyr Arg Gly Thr Thr Phe
                        165                     170                 175

Ala Glu Gly Val Val Ala Phe Leu Ile Leu Pro Gln Ala Lys Lys Asp
                        180                     185                 190

Phe Phe Ser Ser His Pro Leu Arg Glu Pro Val Asn Ala Thr Glu Asp
                        195                     200                 205

Pro Ser Ser Gly Tyr Tyr Ser Thr Thr Ile Arg Tyr Gln Ala Thr Gly
        210                     215                 220

Phe Gly Thr Asn Glu Thr Glu Tyr Leu Phe Glu Val Asp Asn Leu Thr
        225                     230                 235                 240

Tyr Val Gln Leu Glu Ser Arg Phe Thr Pro Gln Phe Leu Leu Gln Leu
                        245                     250                 255

Asn Glu Thr Ile Tyr Thr Ser Gly Lys Arg Ser Asn Thr Thr Gly Lys
                        260                     265                 270

Leu Ile Trp Lys Val Asn Pro Glu Ile Asp Thr Thr Ile Gly Glu Trp
                        275                     280                 285

Ala Phe Trp Glu Thr Lys Lys Asn Leu Thr Arg Lys Ile Arg Ser Glu
                        290                     295                 300

Glu Leu Ser Phe Thr Val Val Ser Asn Gly Ala Lys Asn Ile Ser Gly
        305                     310                 315                 320

Gln Ser Pro Ala Arg Thr Ser Ser Asp Pro Gly Thr Asn Thr Thr Thr
                        325                     330                 335

Glu Asp His Lys Ile Met Ala Ser Glu Asn Ser Ser Ala Met Val Gln
                        340                     345                 350

Val His Ser Gln Gly Arg Glu Ala Ala Val Ser His Leu Thr Thr Leu
                        355                     360                 365

Ala Thr Ile Ser Thr Ser Pro Gln Ser Leu Thr Thr Lys Pro Gly Pro
                        370                     375                 380

Asp Asn Ser Thr His Asn Thr Pro Val Tyr Lys Leu Asp Ile Ser Glu
        385                     390                 395                 400

Ala Thr Gln Val Glu Gln His His Arg Arg Thr Asp Asn Asp Ser Thr
                        405                     410                 415

Ala Ser Asp Thr Pro Ser Ala Thr Thr Ala Ala Gly Pro Pro Lys Ala
                        420                     425                 430
```

-continued

Glu Asn Thr Asn Thr Ser Lys Ser Thr Asp Phe Leu Asp Pro Ala Thr
            435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
            530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
            610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 4
<211> LENGTH: 676
<212> TYPE: PRT
<213> ORGANISM: Sudan (SUDV) glycoprotein from Sudan ebolavirus

<400> SEQUENCE: 4

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
            35                  40                  45

Asp Gln Leu Val Cys Lys Asp His Leu Ala Ser Thr Asp Gln Leu Lys
        50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
            85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly

-continued

```
            115                 120                 125
Val Arg Gly Phe Pro Arg Cys Arg Tyr Val His Lys Ala Gln Gly Thr
            130                 135                 140
Gly Pro Cys Pro Gly Asp Tyr Ala Phe His Lys Asp Gly Ala Phe Phe
145                 150                 155                 160
Leu Tyr Asp Arg Leu Ala Ser Thr Val Ile Tyr Arg Gly Val Asn Phe
                    165                 170                 175
Ala Glu Gly Val Ile Ala Phe Leu Ile Leu Ala Lys Pro Lys Glu Thr
                180                 185                 190
Phe Leu Gln Ser Pro Pro Ile Arg Glu Ala Val Asn Tyr Thr Glu Asn
                    195                 200                 205
Thr Ser Ser Tyr Tyr Ala Thr Ser Tyr Leu Glu Tyr Glu Ile Glu Asn
            210                 215                 220
Phe Gly Ala Gln His Ser Thr Thr Leu Phe Lys Ile Asp Asn Asn Thr
225                 230                 235                 240
Phe Val Arg Leu Asp Arg Pro His Thr Pro Gln Phe Leu Phe Gln Leu
                    245                 250                 255
Asn Asp Thr Ile His Leu His Gln Gln Leu Ser Asn Thr Thr Gly Arg
                260                 265                 270
Leu Ile Trp Thr Leu Asp Ala Asn Ile Asn Ala Asp Ile Gly Glu Trp
                275                 280                 285
Ala Phe Trp Glu Asn Lys Lys Asn Leu Ser Gln Leu Arg Gly Glu
290                 295                 300
Glu Leu Ser Phe Glu Ala Leu Ser Leu Asn Glu Thr Glu Asp Asp
305                 310                 315                 320
Ala Ala Ser Ser Arg Ile Thr Lys Gly Arg Ile Ser Asp Arg Ala Thr
                    325                 330                 335
Arg Lys Tyr Ser Asp Leu Val Pro Lys Asn Ser Pro Gly Met Val Pro
                340                 345                 350
Leu His Ile Pro Glu Gly Glu Thr Thr Leu Pro Ser Gln Asn Ser Thr
                355                 360                 365
Glu Gly Arg Arg Val Gly Val Asn Thr Gln Glu Thr Ile Thr Glu Thr
370                 375                 380
Ala Ala Thr Ile Ile Gly Thr Asn Gly Asn His Met Gln Ile Ser Thr
385                 390                 395                 400
Ile Gly Ile Arg Pro Ser Ser Ser Gln Ile Pro Ser Ser Ser Pro Thr
                    405                 410                 415
Thr Ala Pro Ser Pro Glu Ala Gln Thr Pro Thr Thr His Thr Ser Gly
                420                 425                 430
Pro Ser Val Met Ala Thr Glu Glu Pro Thr Thr Pro Gly Ser Ser
                435                 440                 445
Pro Gly Pro Thr Thr Glu Ala Pro Thr Leu Thr Thr Pro Glu Asn Ile
            450                 455                 460
Thr Thr Ala Val Lys Thr Val Leu Pro Gln Glu Ser Thr Ser Asn Gly
465                 470                 475                 480
Leu Ile Thr Ser Thr Val Thr Gly Ile Leu Gly Ser Leu Gly Leu Arg
                    485                 490                 495
Lys Arg Ser Arg Arg Gln Thr Asn Thr Lys Ala Thr Gly Lys Cys Asn
                500                 505                 510
Pro Asn Leu His Tyr Trp Thr Ala Gln Glu Gln His Asn Ala Ala Gly
            515                 520                 525
Ile Ala Trp Ile Pro Tyr Phe Gly Pro Gly Ala Glu Gly Ile Tyr Thr
            530                 535                 540
```

```
Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
            675
```